(12) United States Patent
Masson

(10) Patent No.: US 10,605,633 B2
(45) Date of Patent: Mar. 31, 2020

(54) DISTRIBUTED SENSOR CALIBRATION

(71) Applicant: Aclima, Inc., San Francisco, CA (US)

(72) Inventor: Nicholas Bantle Masson, Boulder, CO (US)

(73) Assignee: Aclima, Inc., San Francisco, CA (US)

(\*) Notice: Subject to any disclaimer, the term of this patent is extended or adjusted under 35 U.S.C. 154(b) by 673 days.

(21) Appl. No.: 14/878,853

(22) Filed: Oct. 8, 2015

(65) Prior Publication Data

US 2017/0102251 A1    Apr. 13, 2017

(51) Int. Cl.
*G01D 18/00* (2006.01)
*G01D 4/00* (2006.01)
*H04L 29/08* (2006.01)

(52) U.S. Cl.
CPC .......... *G01D 18/00* (2013.01); *G01D 4/004* (2013.01); *G01D 18/008* (2013.01); *H04L 67/12* (2013.01); *Y02B 90/242* (2013.01); *Y02B 90/245* (2013.01); *Y04S 20/322* (2013.01); *Y04S 20/40* (2013.01)

(58) Field of Classification Search
CPC ...................................................... G01D 18/00
See application file for complete search history.

(56) References Cited

U.S. PATENT DOCUMENTS

| | | | | |
|---|---|---|---|---|
| 5,892,690 A | * | 4/1999 | Boatman | G05B 19/042 340/870.02 |
| 6,405,135 B1 | * | 6/2002 | Adriany | F17D 5/02 702/22 |
| 2005/0203360 A1 | * | 9/2005 | Brauker | A61B 5/1468 600/345 |
| 2014/0278144 A1 | | 9/2014 | Risk et al. | |
| 2014/0278186 A1 | * | 9/2014 | Herzl | G01N 33/0006 702/104 |

(Continued)

FOREIGN PATENT DOCUMENTS

| | | |
|---|---|---|
| DE | 102011084264 A1 | 4/2013 |
| WO | 2013083187 A1 | 6/2013 |

(Continued)

OTHER PUBLICATIONS

Moltchanov et al., "On the feasibility of measuring urban air pollution by wireless distributed sensor networks", Science of the Total Environment 502 (2015), available online Oct. 6, 2014, pp. 537-547.\*

(Continued)

*Primary Examiner* — Cory W Eskridge
(74) *Attorney, Agent, or Firm* — Holland & Hart LLP

(57) ABSTRACT

Methods, systems, and devices are described for calibrating a sensor of a distributed sensor system. More specifically, the described features generally relate to calibrating one sensor of such a system using information from one or more other sensors of the system. A calibration model may be determined based at least in part on a difference in geospatial location of the sensors. Further, in the case of one or both sensors being mobile, the difference in geospatial location of the sensors may vary over time such that different calibration models may apply to different portions of the sensed data. Also, the relative quality of the data sensed by the sensors may be taken into account for calibration (e.g., directionality of the calibration).

20 Claims, 7 Drawing Sheets

(56) References Cited

U.S. PATENT DOCUMENTS

| | | | |
|---|---|---|---|
| 2016/0061476 A1* | 3/2016 | Schultz | F24F 11/0017 700/276 |
| 2016/0066068 A1* | 3/2016 | Schultz | G06F 19/327 340/870.07 |
| 2016/0138993 A1* | 5/2016 | Van De Meulenhof | G01L 27/005 702/104 |
| 2016/0153884 A1* | 6/2016 | Han | G01N 1/2205 73/1.06 |
| 2017/0153122 A1* | 6/2017 | Tang | G01C 25/00 |
| 2017/0176034 A1* | 6/2017 | Hussain | F24F 11/006 |
| 2017/0208493 A1* | 7/2017 | Masson | H04B 17/309 |

FOREIGN PATENT DOCUMENTS

| | | |
|---|---|---|
| WO | 2014173414 A1 | 10/2014 |
| WO | 2014198564 A1 | 12/2014 |

OTHER PUBLICATIONS

Takruri et al., "Distributed Recursive Algorithm for Auto Calibration in Drift Aware Wireless Sensor Networks", Innovations and Advanced Techniques in Sytems, Computing Sciences and Software Engineering, Dec. 2008, pp. 21-25.*

Ikram et al., "View: implementing low ost air quality monitoring solution for urban areas", Environmental Systems Research, Dec. 2012, 8 pages.*

Bychkovskiy et al., "A Collaborative Approach to In-Place Sensor Calibration", F. Zhao and L. Guibas (Eds.): IPSN 2003, LNCS 2634, Dec. 2003, pp. 301-316.*

Ramboz, John D. and Federman, Charles, Evaluation and Calibration of Mechanical Shock Accelerometers by Comparison Methods, Mar. 1974, National Bureau of Standards. (Year: 1974).*

Vogler, Chris, Calibration of Accelerometer Vibration Sensitivity by Reference, Apr. 5, 2015, Department of Electrical and Computer Engineering, MSU. (Year: 2015).*

Honicky, Jr., "Towards a societal scale, mobile sensing system," Feb. 1, 2011, 133 pgs., Technical Report No. UCB/EECS-2011-9, http://www.eecs.berkeley.edu/Pubs/TechRpts/2011/EECS-2011-9.html, Electrical Engineering and Computer Sciences University of California at Berkeley.

Xiang et al., "Collaborative Calibration and Sensor Placement for Mobile Sensor Networks," 2012 ACM/IEEE 11th International Conference on Information Processing in Sensor Networks (IPSN), Beijing, Apr. 16-20, 2012, pp. 73-83, Institute of Electrical and Electronics Engineers.

Piedrahita et al., "The next generation of low-cost personal air quality sensors for quantitative exposure monitoring," Atmos. Meas. Tech., 7, 3325-3336, Oct. 2014 www.aimos-meas-iech.net/7/3325/2014/doi:10.5194/amt-7-3325-2014, Atmospheric Measurement Techniques.

Masson et al., "Approach for quantification of metal oxide type semiconductor gas sensors used for ambient air quality monitoring," Mar. 1, 2015, pp. 339-345, vol. 208, Sensors and Actuators B: Chemical, ScienceDirect, Elsevier.

* cited by examiner

DISTRIBUTED SENSOR CALIBRATION

BACKGROUND

Field of the Disclosure

The present disclosure, for example, relates to calibrating sensors of a distributed sensor system, and more particularly to calibrating one sensor using information from one or more other sensors.

Description of Related Art

Distributed sensor systems may be deployed to collect data over an area or areas of interest. For example, environmental data (e.g., data including measurements of environmental conditions) may be collected using a plurality of sensor assemblies in different physical locations of such area(s) of interest. Such systems may employ relatively low cost sensors, which generally may provide lower quality data than scientific-grade instruments, for instance. Further, the sensors of such systems may be subject to outdoor conditions, and may suffer from decay and/or drifting, for example.

Calibration of environmental sensors may be important to ensure that data collected is useful for a particular purpose (e.g., accurate, reliable, etc.). This is particularly true when aggregating data from a plurality of sensors as in a distributed sensor system. However, calibration may be difficult and complex, particularly when the system includes sensors of different types and/or from different manufacturers. Employing on-site calibration, known automated calibration systems, or a reference standard for each sensor of the system may be cost prohibitive.

SUMMARY

The described features generally relate to one or more improved systems, methods, and/or apparatuses for calibrating sensors of a distributed sensor system. More specifically, the described features generally relate to calibrating one sensor of such a system using information from one or more other sensors of the system. A calibration model may be determined based at least in part on a difference in geospatial location of the sensors. Further, in the case of one or both sensors being mobile, the difference in geospatial location of the sensors may vary over time such that different calibration models may apply to different portions of the sensed data. Also, the relative quality of the data sensed by the sensors, which may be related to the sensors themselves or other conditions affecting the data, may be taken into account for calibration (e.g., directionality of the calibration).

A method for calibrating an environmental sensor is described. The method may include: collecting sensed data from a first environmental sensor and a second environmental sensor of the distributed environmental sensor system; determining a difference in geospatial location between a location of the first environmental sensor and a location of the second environmental sensor; determining a calibration model based at least in part on the determined difference in geospatial location; and, calibrating the first environmental sensor using the determined calibration model and the sensed data of the second environmental sensor.

In some aspects, calibrating the first environmental sensor may involve correlating the sensed data of the first environmental sensor with the sensed data of the second environmental sensor.

In some aspects, calibrating the first environmental sensor may involve performing a frequency-based decomposition or frequency-based filtering of the sensed data of the first and second environmental sensors. In such examples, determining the calibration model may involve selecting a portion of the decomposed or filtered data of the first environmental sensor and a portion of the decomposed data of the second environmental sensor. Such selection may be based at least in part on the determined difference in geospatial location. Further, calibrating the first environmental sensor may involve correlating or setting equal the selected portions of the decomposed or filtered data of the first and second environmental sensors.

In some aspects, the method may include determining a difference in a quality between the sensed data of the first environmental sensor and a quality of the sensed data of the second environmental sensor. A directionality of the calibration may be determined based at least in part on the determined difference in the quality. For example, the calibration of the first environmental sensor may occur when the quality of the sensed data of the first environmental sensor is lower than the quality of the sensed data of the second environmental sensor. The quality of the sensed data of at least one of the first environmental sensor and the second environmental sensor may be based at least in part on an amount of the sensed data provided by that environmental sensor, a data history of that environmental sensor, a periodicity of data provided by that environmental sensor, a calibration history of that environmental sensor, or a predetermined characteristic of that environmental sensor.

In some aspects, calibrating the first environmental sensor may involve selecting a portion of the sensed data of the first environmental sensor and a corresponding portion of the sensed data of the second environmental sensor based at least in part on the determined difference in geospatial location over time.

In some aspects, the method may include determining a secondary parameter that affects the sensed data of the first environmental sensor. In such case, the sensed data of the first environmental sensor may be adjusted based on an effect of the parameter, with the adjustment being performed prior to performing the calibration. In various examples, a secondary parameter may be determined at a calibration device, provided to the calibration device by one or more sensors, or otherwise provided to the calibration device.

In some aspects, the method may involve calibrating the second environmental sensor using the determined calibration model and the sensed data of the first environmental sensor.

A calibration device for calibrating an environmental sensor of a distributed environmental sensor system is described. The apparatus may include a processor and memory communicatively coupled with the processor. The memory may include computer-readable code that, when executed by the processor, causes the device to: collect sensed data of a first environmental sensor and a second environmental sensor of the distributed environmental sensor system; determine a difference in geospatial location between a location of the first environmental sensor and a location of the second environmental sensor; determine a calibration model based at least in part on the determined difference in geospatial location; and, calibrate the first environmental sensor using the determined calibration model and the sensed data of the second environmental sensor. The memory may include computer-readable code that, when executed by the processor, causes the device to perform features of the method described above and further herein.

A non-transitory computer-readable medium is described. The medium may include computer-readable code that, when executed, causes a device to: collect sensed data of a first environmental sensor and a second environmental sensor of the distributed environmental sensor system; determine a difference in geospatial location between a location of the first environmental sensor and a location of the second environmental sensor; determine a calibration model based at least in part on the determined difference in geospatial location; and, calibrate the first environmental sensor using the determined calibration model and the sensed data of the second environmental sensor. The medium may include computer-readable code that, when executed, causes a device to perform features of the method described above and further herein.

The foregoing has outlined rather broadly the features and technical advantages of examples according to the disclosure in order that the detailed description that follows may be better understood. Additional features and advantages will be described hereinafter. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, both their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present invention may be realized by reference to the following drawings. In the appended figures, similar components or features may have the same reference label. Further, various components of the same type may be distinguished by following the reference label by a dash and a second label that distinguishes among the similar components. If only the first reference label is used in the specification, the description is applicable to any one of the similar components having the same first reference label irrespective of the second reference label.

DETAILED DESCRIPTION

This description discloses techniques for calibrating a sensor of a distributed sensor system. The described calibrating techniques use a calibration model and sensed data of another sensor of the system. The calibration model may be determined based at least in part on a difference in geospatial location between a location of the sensor to be calibrated and a location of the sensor to be used for calibration. Further, a portion of the sensed data of the sensor to be calibrated and a corresponding portion of the sensed data of the other sensor may be selected for performing the calibration. Such selection may be based at least in part on the determined difference in geospatial location.

Various calibration models may be used to correlate the sensed data of the sensor being calibrated with the sensed data of the other sensor. For example, calibrating the sensor may involve a frequency-based decomposition or frequency-based filtering of the sensed data of both sensors. Based at least in part on the determined difference in geospatial location, a calibration model may be selected that employs a relatively low frequency decomposition or filtering of the sensed data for correlation, a relatively high frequency decomposition or filtering of the sensed data for correlation, or both. Various calibration models may be used to adjust how sensed data of an environmental condition is reported from a physical measurement at a sensor. For instance, a calibration model may perform an adjustment to a sensor gain, a sensor gain exponent, a sensor offset, or any other parameter or combination of parameters used by a sensor or sensor system to convert a measurement to a reported condition. Such adjustments may be made directly at a sensor, at a portion of a sensor assembly that contains the sensor, or at any other device that receives sensed data from the sensor. Through various examples, these calibration models can be applied to improve correlation between sensors in a distributed sensor system and provide higher quality data from the system.

The following description provides examples, and is not limiting of the scope, applicability, or examples set forth in the claims. Changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. Also, features described with respect to some examples may be combined in other examples.

Figure 1:
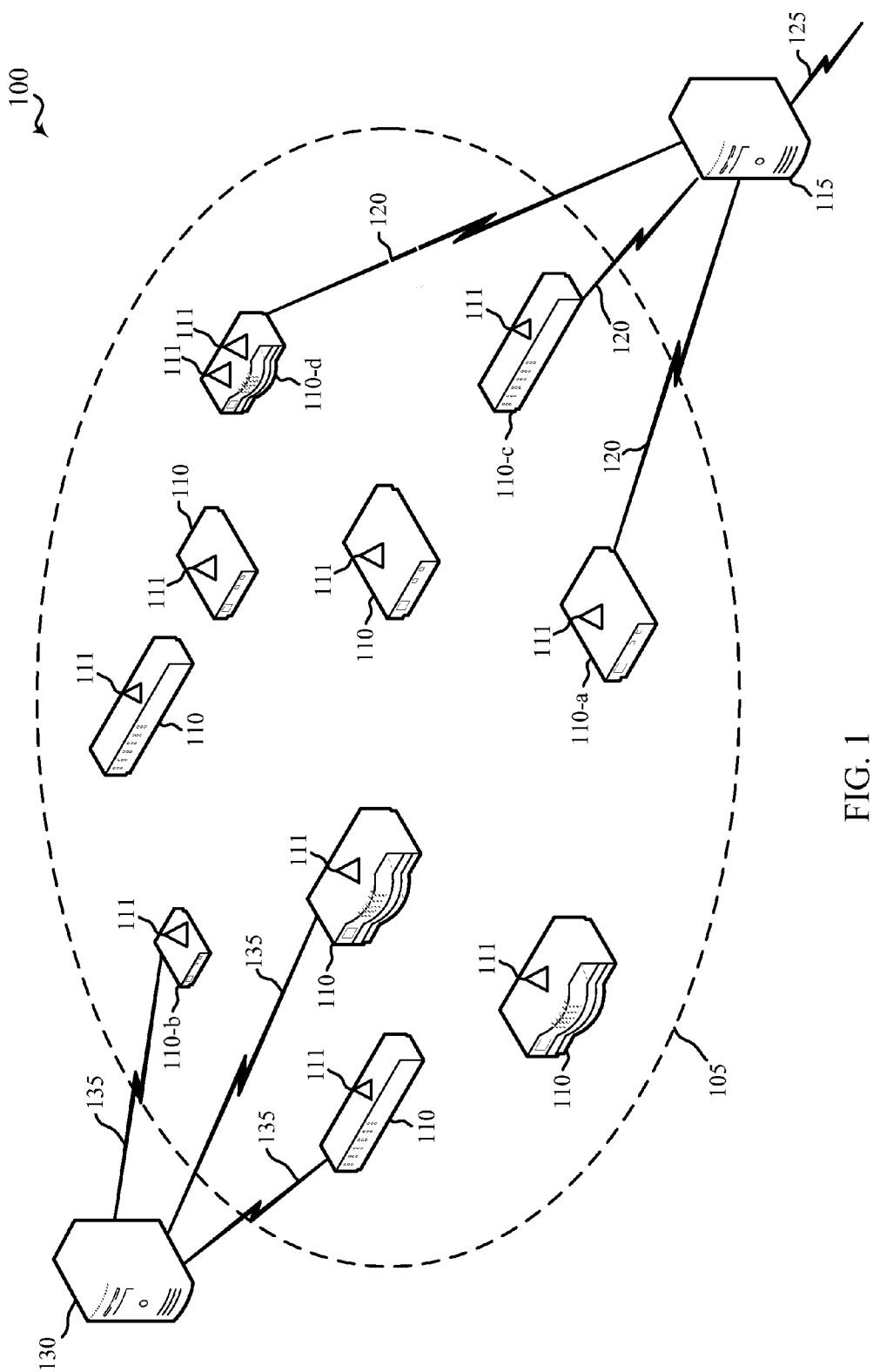
FIG. 1 shows a block diagram of a distributed sensor system and a calibration device associated therewith, in accordance with various aspects of the present disclosure.

Referring first to FIG. 1, a block diagram illustrates an example of a distributed sensor system 100 in accordance with various aspects of the present disclosure. The distributed sensor system 100 may include a plurality of sensor assemblies 110 distributed over an area of interest 105, and a central processing device 115. The sensor assemblies 110 may be, for example, configured to monitor and/or assess environmental conditions that affect air quality, such as carbon monoxide, carbon dioxide, nitrogen oxides, sulfur dioxide, particulates, etc. To support such measurements, each of the sensor assemblies 110 may include one or more sensors 111, such as sensor assembly 110-*a* having a single sensor and sensor assembly 110-*d* having a plurality of sensors. The sensors 111 may measure different environmental conditions and/or may measure some of the same environmental conditions using the same or disparate technologies. Also, the sensors 111 or the sensor assemblies 110 may be of different quality and/or may provide sensed data that is of different quality, or is characterized by different qualities.

Each of the sensor assemblies 110 may be associated with one or more environmental conditions that are communicated in the distributed sensor system 100. For instance, a sensor assembly 110 may transmit sensed data by way of a wired or wireless communication system. Thus, each sensor assembly 110 may include hardware and/or software to provide communication through the distributed sensor system 100. For example, each sensor assembly 110 may communicate with the central processing device 115 via wireless links 120 using any suitable wireless communication technology, or via a wired link (not shown). Although wireless links 120 are not shown between each of the sensor assemblies 110 and the central processing device 115 for the sake of simplicity, it should be understood that the central processing device 115 may communicate with all of the sensor assemblies 110 of the system 100, which may include wired or wireless communication links from one of the sensor assemblies 110, through another of the sensor assemblies 110, and eventually to the central processing device 115.

The central processing device 115 can receive sensed data from the sensor assemblies 110, and provide various functions. For instance, the central processing device 115 may aggregate data and perform various calculations with the received data. In some examples the central processing device 115 can perform reporting or alerting functions based on the received data. In some examples the central processing device 115 may include a calibration model for one or more sensors 111 that provide sensed data to the central processing device. In this way, calibration models may be stored at a central location, which may be in addition to, or instead of a calibration model stored locally at a sensor 111 or a sensor assembly 110. In some examples the central processing device 115 can transmit any of the received data, calculations made from the received data, reports, or alerts to one or more external devices by way of an external communication link 125.

Each of the sensor assemblies 110 may also measure secondary parameters that may or may not be related to the environmental conditions that are communicated through the network. In some examples, secondary parameters may support the measurement and/or calculation of environmental conditions that are communicated through the network. For example, the measurement of an atmospheric concentration of a particular gas may require secondary measurements of temperature and/or atmospheric pressure, in addition to a sensor 111. In some examples, the calibration of a sensor 111 associated with an environmental condition may be a function of a secondary parameter. For instance, a sensor gain or sensor offset for a sensor 111 that measures a concentration of an atmospheric constituent may be based on temperature. In such examples, a sensor assembly 110 that reports the concentration of the atmospheric constituent to the network may also measure temperature in order to validate, or otherwise determine a quality of the reported data.

In other examples, a sensor assembly 110 may measure secondary parameters that are not directly related to the measurement or calculation of an environmental condition, but are otherwise related to supporting the functionality of the sensor assembly 110. For instance, secondary parameters measured by the sensor assembly 110 may further include a sensor assembly power level, a sensor assembly battery charge level, a communication throughput, a network status parameter, clock time, sensor run time, or any other secondary parameter related to supporting the operation of the sensor assembly 110.

A calibration device 130 is also illustrated in FIG. 1. As shown, the calibration device 130 may communicate with the sensor assemblies 110 via wireless communication links 135 using any suitable wireless communication technology, or via a wired link (not shown). Although wireless communication links 135 are not shown between each of the sensor assemblies 110 and the calibration device 130 for the sake of simplicity, it should be understood that the calibration device 130 may communicate with all of the sensor assemblies 110 of the system 100, which may include wired or wireless communication links from one of the sensor assemblies 110, through another of the sensor assemblies 110, and eventually to the calibration device 130. Furthermore, although the calibration device 130 and the central processing device 115 are shown as separate devices, in various examples the two devices, or any of the described functionality of the two devices, may be embodied in the same device.

The calibration device 130 may receive sensed data from sensors 111 as transmitted by the sensor assemblies 110, as well as an identity of each sensor 111 and/or sensor assembly 110 that is associated with the respective sensed data. In some examples the calibration device 130 may determine a location of a sensor 111 by looking up a predetermined location stored in memory associated with the calibration device 130. In some examples the calibration device 130 may receive information associated with the location of a sensor 111, which may be received from a central database, such as a database stored at the central processing device 115, or received from the sensor assembly 110 that includes the sensor 111. In examples where the sensor assembly 110 transmits location information for a sensor 111, the location information may be predetermined information stored at the sensor assembly 110, or may be otherwise measured by the sensor assembly 110. For instance, in some examples the sensor assembly 110 may be configured to determine its own location by receiving signals from a GPS or GLONASS satellite constellation, or any terrestrial or satellite-based system that provides positioning signals. In some examples, the location of the sensor 111 as determined by the sensor assembly 110 can be transmitted to the calibration device 130.

As discussed in further detail below, the calibration device 130 may determine a calibration model for one or more of the sensors 111. In some examples the calibration device 130 may transmit an instruction to adjust a parameter associated with the calibration of a sensor 111. For instance, the calibration device 130 may communicate calibration information (e.g., adjustments, offsets, corrections, etc.) to the respective sensor assemblies 110 to improve the correlation of the sensed data of the sensors 111, where the calibration adjustments may take place at one or both of the sensor itself, or at another portion of the sensor assembly 110 that is associated with converting an output or a sensor 111 to data representing an environmental condition. In some examples, calibration information for a plurality of sensors 111 may be communicated to the central processing device 115, and the central processing device 115 can use calibration information to adjust sensed data from the plurality to improve correlation between sensors 111 that measure the same environmental condition.

The calibration device 130 may be configured to determine a difference in geospatial location between sensors 111 and then determine a calibration model to use for calibration of the sensors 111. For example, the calibration device 130 may determine that one of the sensor assemblies 110-*a* is at a relatively far distance (e.g., 1 kilometer) or proximity to another of the sensor assemblies 110-*b*. The relatively far distance/proximity may allow a calibration model to be used that correlates portions the sensed data from a sensor 111 of the sensor assembly 110-*a* reflecting a relatively steady state, or having relatively low frequency changes with corresponding sensed data from a sensor 111 of the sensor assembly 110-*b*. Alternatively, the calibration device 130 may determine that a different sensor assembly 110-*c* is at a relatively close distance (e.g., 1 meter) or proximity to the sensor assemblies 110-*a*. The relatively close distance/proximity may allow a calibration model to be used that correlates the sensed data from a sensor 111 of the sensor assembly 110-*a* including both steady state conditions and some amount of transient behavior, or otherwise relatively higher frequency changes with corresponding sensed data from a sensor 111 of the sensor assembly 110-*c*.

In some examples, the sensors 111 may be cross-calibrated (e.g., calibrating a sensor 111 of the sensor assembly 110-*a* using the sensed data from a sensor 111 of the sensor assembly 110-*b*, and calibrating the sensor assembly 110-*b* using the sensed data of the sensor assembly 110-*a*). However, a directionality of the calibration may be determined by the calibration device 130, for example, based at least in part on a difference in a quality of the sensed data of the sensors 111, where the quality of the sensed data may have a clear direction indicating a relationship from higher to lower quality, or the quality of the sensed data may reflect a particular characteristic of the sensed data.

In some examples, a first sensor 111 may be known by a calibration device 130 to be a scientific-grade instrument that has well-known and/or precisely calibrated sensor characteristics such as gain or offset. A second sensor 111 may be known by the calibration device 130 to be a lower-grade instrument characterized by greater uncertainty with respect to the sensor characteristics such as gain or offset. In other examples the grades of the first sensor 111 and the second sensor 111 may be otherwise provided to the calibration device 130, such as a transmission from a sensor assembly 110 having the sensor 111. In such examples the calibration device 130 may determine that the sensed data from the first sensor 111 has a higher quality than sensed data from the second sensor 111, based on the grades of the sensors 111 and/or the sensor assemblies 110 that include each sensor 111.

In some examples, a difference in quality may be related to an age of a sensor 111 or an age of a sensor assembly 110 that includes a sensor 111. For example, a first sensor 111 may be older than a second sensor 111, and the first sensor 111 may have a known or unknown level of drift, reduced sensitivity, and/or fouling. In such examples a calibration device 130 may determine that sensed data from the second sensor 111 has a higher quality than sensed data from the first sensor 111, based on the known ages of the sensors 111.

In some examples, a difference in quality may be related to a characteristic of the sensed data from the first and second sensors 111. For example, the first and second sensors 111 may be identically constructed, and or be part of identically constructed sensor assemblies 110, but sensed data from the first sensor 111 may have greater signal noise than sensed data from the second sensor 111. In such examples a calibration device 130 may determine that sensed data from the second sensor 111 has a higher quality than sensed data from the first sensor 111, based on the known level of noise in the sensed data from each of the sensors 111.

In some examples, a difference in quality may be related to an amount of data. For example, a first sensor 111 and a second sensor 111 may be identically constructed, but the first sensor 111 may have been deployed earlier than the second sensor 111, and sensed data from the first sensor 111 may have a greater validation history than sensed data from the second sensor 111. In such examples a calibration device 130 may determine that sensed data from the first sensor 111 has a higher quality than sensed data from the second sensor 111, based on the known amount of sensed data from each of the sensors 111.

In some examples, a difference in quality may be related to a periodicity of data. For example, first and second sensors 111 may be configured to measure data at different rates, or during different time periods. In examples where sampling rates are different, it may be suitable to use data from a sensor 111 having a higher sampling rate to contribute to the calibration of a sensor 111 having a lower sampling rate, but not vice-versa. In some examples where a first sensor 111 measures an environmental condition continuously and a second sensor 111 measures the environmental condition intermittently, or experiences data drop-outs, it may be suitable to use data from the first sensor 111 to contribute to the calibration of the second sensor 111, but not vice versa. Thus, in either case, the calibration device 130 can ascribe a quality to each of the sensors 111, and determine a difference in the quality of sensed data based on the periodicity of the sensed data The directionality of the calibration may be from a sensor 111 associated with higher quality sensed data to a sensor 111 associated with lower quality sensed data, for example. However, even though one sensor 111 may have higher quality components or construction than another sensor 111, the sensor having higher quality components or construction may be calibrated using the sensed data of a sensor having lower quality components or construction when the lower quality sensor provides sensed data having higher quality, or a particular quality. In other examples, the directionality of calibration may include a direction from a sensor 111 associated with lower quality sensed data to a sensor 111 associated with higher quality sensed data, but the calibration effect or magnitude may be reduced as compared to a higher-to-lower quality directionality.

Figure 2:
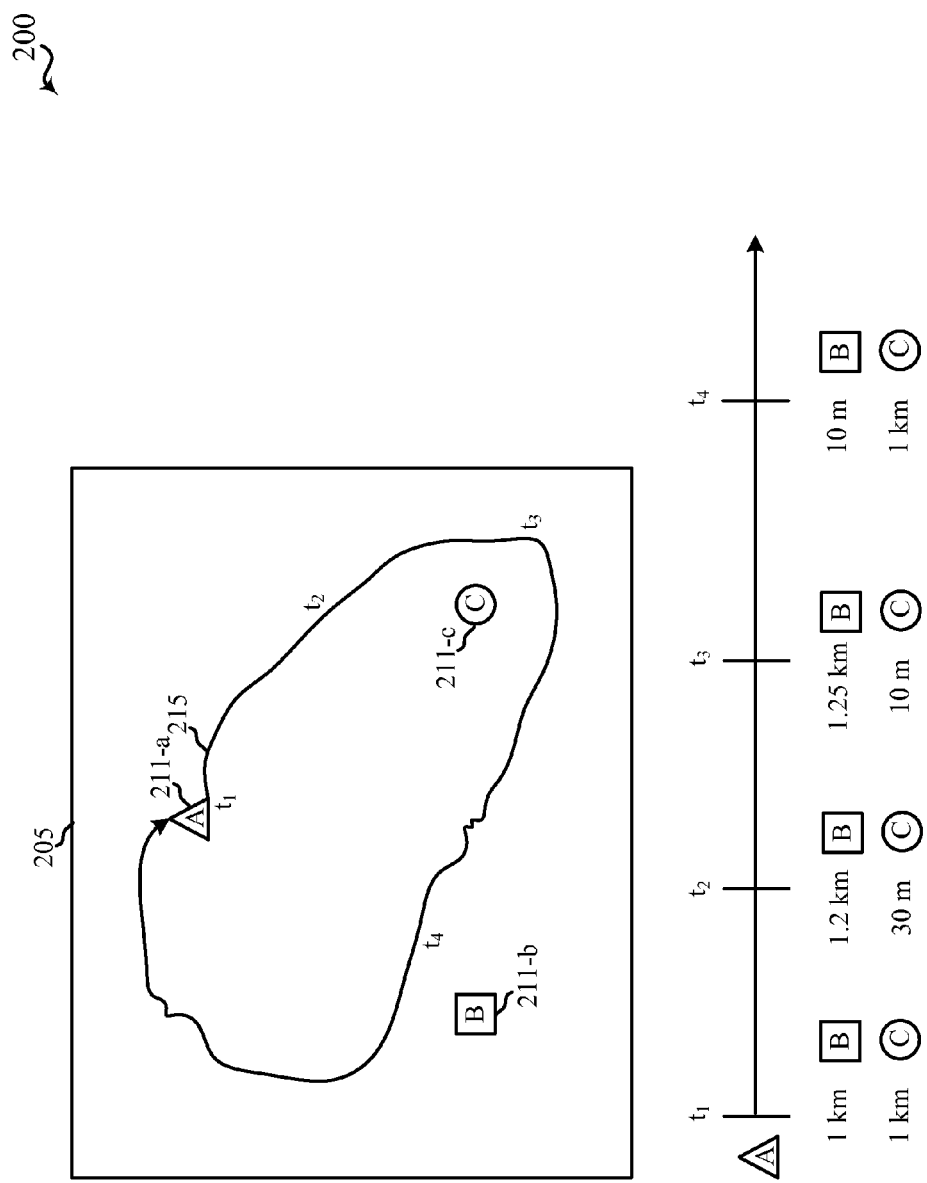
FIG. 2 shows a diagram illustrating a time varying difference in geospatial location between sensor assemblies, in accordance with various aspects of the present disclosure.

FIG. 2 shows a diagram 200 illustrating a time varying difference in geospatial location between sensors 211, in accordance with various aspects of the present disclosure. The diagram 200 depicts sensors 211 (denoted A, B and C) of a distributed sensor system, distributed within an area of interest 205. In this example, the sensors B and C are fixed-position sensors 211, while the sensor 211-*a* is a mobile sensor 211 that traverses a path 215 over time. The diagram 200 further depicts a timeline for the travel of the sensor 211-*a* showing relative distances from the sensors 211-*b* and 211-*c*.

As shown, sensor 211-*a* may begin at an initial location that is approximately 1 kilometer (km) from each of sensors 211-*b* and 211-*c* at time $t_1$. In this example, the 1 km difference in location between the location of sensor 211-*a* and the locations of sensors 211-*b* and 211-*c* may require sensor 211-*a* to be calibrated using a relatively low frequency decomposition or filtering of the sensed data of sensors 211-*b* or 211-*c* (or both), or vice versa. The low frequency decomposition may include, for instance, sensed data that has been passed through a low-pass filter (which may vary in type depending on the nature of the data) with a relatively low frequency. Thus, the sensed data used for calibration around time $t_1$ may be limited to data that represents a relatively steady-state condition, where transients or other relatively high-frequency phenomena are removed or reduced. Alternatively, for instance, a fast Fourier transform (FFT) or similar frequency decomposition may be employed to remove the time domain aspect of the data. After passing through the FFT, the magnitude of the signal constituents may be correlated. In other examples, the distance between two sensors may dictate that a decomposition simply excludes sensed data from being used in a calibration process when the distance is above a predetermined threshold.

As the sensor 211-a traverses the path 215, the sensor 211-a moves closer to the sensor 211-c, but remains relatively far from the sensor 211-b, such as at time $t_2$. In this example, the 1.2 km difference between the location of sensor 211-a and the location of sensor 211-b may still require sensor 211-a to be calibrated using a relatively low frequency decomposition or filtering of the sensed data of sensor 211-b, or vice versa. However, the 30 meter (m) difference between the location of sensor 211-a and the location of sensor 211-c may permit an incrementally higher frequency decomposition or filtering of the sensed data of sensor 211-c for calibrating sensor 211-a, or vice versa. For instance, in examples where decomposition or filtering is associated with a low pass filter, a cutoff frequency for decomposing or filtering data for calibration between sensors 211-a and C may be higher than a cutoff frequency for decomposing or filtering data for calibration between sensors 211-a and 211-b. Thus, the relatively higher frequency decomposition of the sensed data of sensor 211-c may be used for calibrating sensor 211-a, or vice versa. The sensed data used for calibration at this point may include data that is sensed around the time $t_1$ as well as data that is sensed around the time $t_2$ under circumstances where the calibration model has not changed (e.g., low frequency decomposition or filtering). In some cases, however, the sensed data used for calibration at this point may be limited to data that is sensed around the time $t_2$, for example, because of differences between the surroundings (e.g., topography) of sensor 211-a at times $t_1$ and $t_2$.

At time $t_3$, sensor 211-a moves still closer to sensor 211-c, but remains relatively far from sensor 211-b. In this example, the 10 m difference in location between the location of sensor 211-a and the location of sensor 211-c may be small enough to use a relatively high frequency decomposition or filtering of the sensed data of sensor 211-c for calibrating sensor 211-a, or vice versa. For instance, as compared to time $t_2$, a cutoff frequency associated with a low-pass filter can be even higher, or the sensed data may even be used in an unfiltered condition for use in a calibration model. The sensed data used for such calibration at this point may be limited to data that is sensed around the time $t_3$ while the difference in location (A-C) remains about the same.

Also at time $t_3$, the 1.25 km and 10 m differences in location between the location of sensor 211-a and the locations of sensors 211-b and 211-c may allow sensor 211-a to be calibrated using the relatively low frequency decomposition of the sensed data of sensors 211-b or 211-c (or both), or vice versa. Such calibration at this point may use data that is sensed around the time $t_1$ and/or data that is sensed around the time $t_2$ as well as data that is sensed around the time $t_3$, depending on any differences between the surroundings the of sensor 211-a at times $t_1$, $t_2$ and $t_3$.

At time $t_4$, sensor 211-a moves closer to sensor 211-b, but moves further away from sensor 211-c. In this example, the 10 m difference in location between the location of sensor 211-a and the location of sensor 211-b may be small enough to use a relatively high frequency decomposition of the sensed data of sensor 211-b for calibrating sensor 211-a, or vice versa. The sensed data used for such calibration at this point may be limited to data that is sensed around the time $t_4$ while the difference in location (A-B) remains about the same.

Also at time $t_4$, the 10 m and 1 km differences in location between the location of sensor 211-a and the locations of sensors 211-b and 211-c may allow sensor 211-a to be calibrated using the relatively low frequency decomposition of the sensed data of sensors 211-b or 211-c (or both), or vice versa. Such calibration at this point may use data that is sensed around the time $t_1$, around the time $t_2$, and/or around the time $t_3$ as well as data that is sensed around the time $t_4$, depending on any differences between the surroundings the of the sensor 211-a at times $t_1$, $t_2$, $t_3$ and $t_4$.

It should be understood that the number of sensors 11, whether fixed-position or mobile, may vary and that the sensor arrangement depicted in FIG. 2 is only an example. Further, it should be understood that the path 215 as well as the differences in locations set forth (1 km, 1.2 km, 1.25 km, 30 m and 10 m) are only for purpose of illustration, and that differences in geospatial locations between sensors 211 may vary in practice and values of such differences for determining which calibration model to use may be determined for a particular implementation and/or may vary (e.g., based at least in part on topography).

Figure 3A:
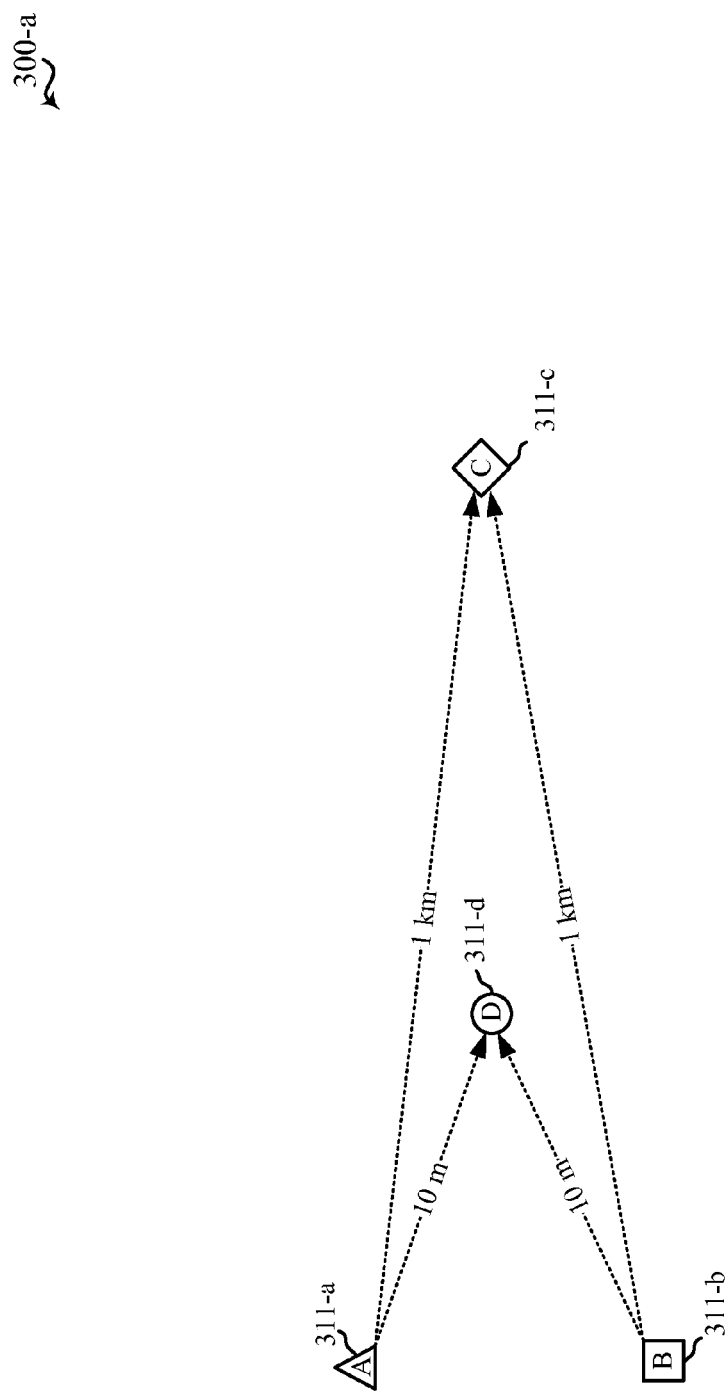
FIG. 3A shows a diagram illustrating frequency-based filtering of sensed data, in accordance with various aspects of the present disclosure.

FIG. 3A shows a diagram 300-a illustrating a plurality of sensors 311 (denoted A, B, C and D) of a distributed sensor system, in accordance with various aspects of the present disclosure. For the sake of example and clarity, the sensors 311 may be fixed-location sensors. However, it should be understood that mobility of one or more of the sensors 311 is also possible, such as described above with respect to FIG. 2.

The diagram 300-a provides an example of how a difference in geospatial location may be used to determine a calibration model for calibrating one or more of the sensors. As shown, a difference in geospatial location between a location of sensor 311-a and a location of sensor 311-c is 1 km. A difference in geospatial location between a location of sensor 311-b and a location of sensor 311-c is also 1 km. The 1 km difference may be equal to or less than a first threshold difference in geospatial location, for which a first calibration model may be used in conjunction with sensed data of sensors 311-a and/or 311-b and 311-c. The first calibration model may be used to calibrate sensor 311-c using the sensed data of sensor 311-a and/or the sensed data of sensor 311-b. Further, the first calibration model may be used to calibrate sensor 311-a or sensor 311-b using the sensed data of sensor 311-c. Thus, calibration at a given time "t" may involve multiple sets of sensed data, allowing for sequential calibration of a sensor or combined one-off calibration, etc.

Further, a difference in geospatial location between a location of sensor 311-a and a location of sensor 311-d is 10 m. A difference in geospatial location between a location of sensor B and a location of sensor 311-d is also 10 m. The 10 m difference may be equal to or less than a second threshold difference in geospatial location, for which a second calibration model may be used in conjunction with sensed data of sensors 311-a and/or 311-b and 311-d. The second calibration model may be used to calibrate sensor 311-*d* using the sensed data of sensor 311-*a* and/or the sensed data of sensor 311-*b*. Further, the second calibration model may be used to calibrate sensor 311-*a* or sensor 311-*b* using the sensed data of sensor 311-*d*.

Figure 3B:
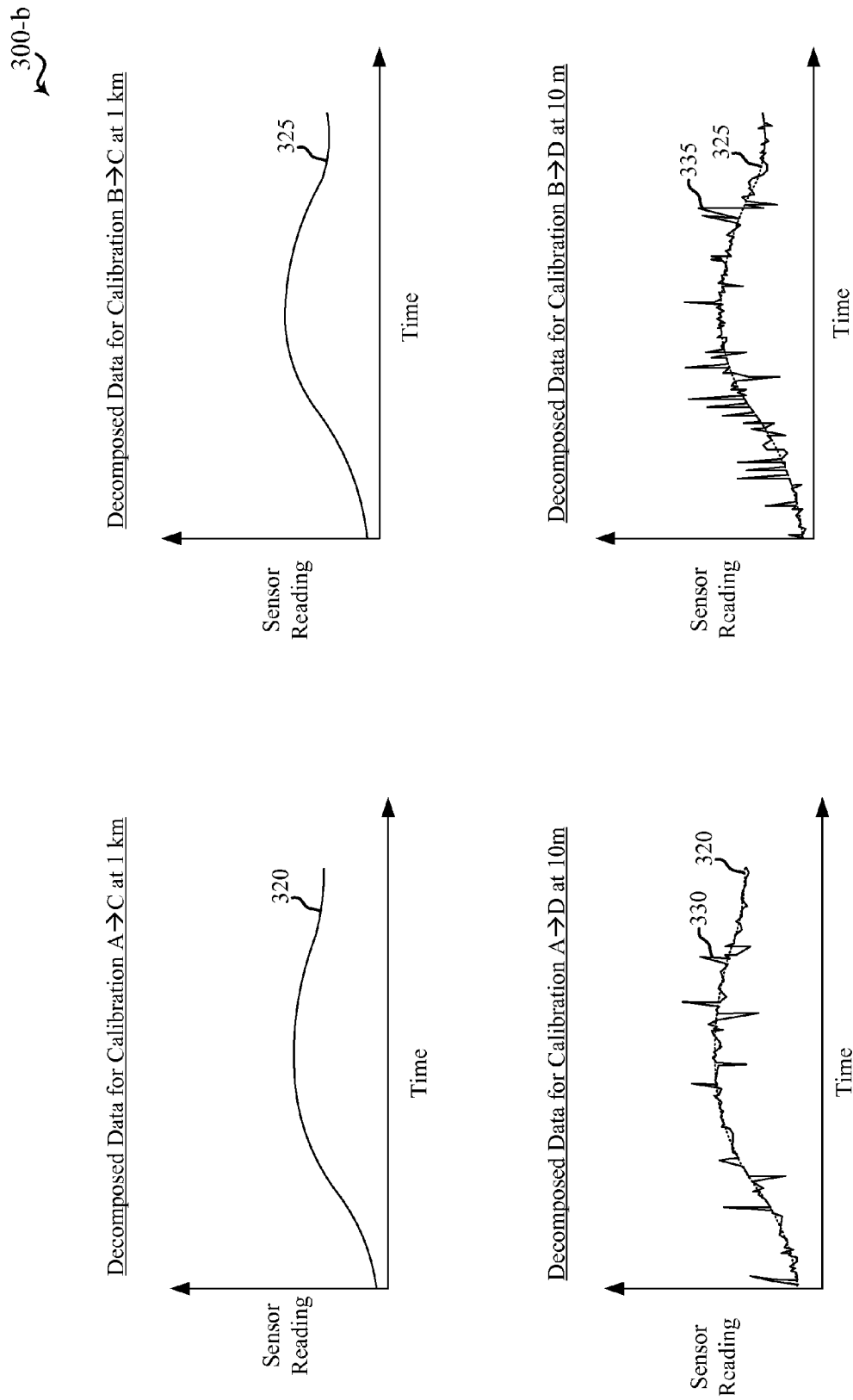
FIG. 3B shows a diagram illustrating frequency-based filtering of sensed data and calibration models for the sensors depicted in FIG. 3A, in accordance with various aspects of the present disclosure.

FIG. 3B shows a diagram 300-*b* illustrating frequency-based decomposition of sensed data and calibration models for the sensors depicted in FIG. 3A, in accordance with aspects of the present disclosure. Thus, references to sensor A, sensor B, sensor C and sensor D correspond to sensors 311-*a*, 311-*b*, 311-*c* and 311-*d*, respectively, as described above with reference to FIG. 3A.

The graphical plot entitled "Decomposed Data for Calibration A→C at 1 km" illustrates a frequency-based filtering 320 of sensed data (sensor reading) of sensor 311-*a* that may be used for calibrating sensor 311-*c*. As shown, the frequency-based filtering 320 of the sensed data of sensor 311-*a* includes relatively low frequency component (solid line depicting relatively infrequent/gradual changes in sensed data). As discussed above with respect to FIG. 3A, the 1 km difference in geospatial location between sensor 311-*a* and sensor 311-*c* may be equal to or less than a threshold difference in geospatial location, for which the frequency-based filtering 320 of sensed data from sensor 311-*a* may be used for a calibration model applied to sensor 311-*c*.

Similarly, the graphical plot entitled "Decomposed Data for Calibration B→C at 1 km" illustrates a frequency-based filtering 325 of sensed data (sensor reading) of sensor 311-*b* that may be used for calibrating sensor 311-*c*. As shown, the frequency-based filtering 325 of the sensed data of sensor 311-*b* includes relatively low frequency component (solid line depicting relatively infrequent/gradual changes in sensed data). In some examples the relatively low-frequency component of two sensors that are relatively closely spaced may be similar, or substantially the same, such as shown by the frequency-based decompositions 320 and 325. As discussed above with respect to FIG. 3A, the 1 km difference in geospatial location between sensor 311-*a* and sensor 311-*c* may be equal to or less than a threshold difference in geospatial location, for which the frequency-based decomposition 325 of sensed data from sensor 311-*b* may be used for a calibration model applied to sensor 311-*c*.

The graphical plot entitled "Decomposed Data for Calibration A→D at 10 m" illustrates a frequency-based filtering 330 of sensed data (sensor reading) of sensor 311-*a* that may be used for calibrating sensor 311-*d*. As shown, the frequency-based filtering 330 of the sensed data of sensor 311-*a* includes higher-frequency content that is not reflected in the frequency-based filtering 320, shown in the present graph for reference. The relatively higher frequency content may be appropriate in some examples because sensor 311-*d* is located more closely to sensor 311-*a* than sensor 311-*c* is located to sensor 311-*a*. As discussed above with respect to FIG. 3A, the 10 m difference in geospatial location between sensor 311-*a* and sensor 311-*d* may be equal to or less than the second threshold difference in geospatial location, for which the frequency-based filtering 330 of sensed data from sensor 311-*a* may be used for a calibration model applied to sensor 311-*d*.

The graphical plot entitled "Decomposed Data for Calibration B→D at 10 m" illustrates a frequency-based filtering 335 of sensed data (sensor reading) of sensor 311-*b* that may be used for calibrating sensor 311-*d*. As shown, the frequency-based filtering 335 of the sensed data of sensor 311-*b* includes higher-frequency content that is not reflected in the frequency-based filtering 325, shown in the present graph for reference. In some examples the relatively higher-frequency component of two sensors that are relatively closely spaced may be not necessarily be similar, such as the differences shown by the frequency-based decompositions 330 and 335. The relatively higher frequency content may be appropriate in some examples because sensor 311-*d* is located more closely to sensor 311-*b* than sensor 311-*c* is located to sensor 311-*b*. As discussed above with respect to FIG. 3A, the 10 m difference in geospatial location between sensor 311-*b* and sensor 311-*d* may be equal to or less than the second threshold difference in geospatial location, for which the frequency-based decomposition 335 of sensed data from sensor 311-*b* may be used for a calibration model applied to sensor 311-*d*.

Figure 4A:
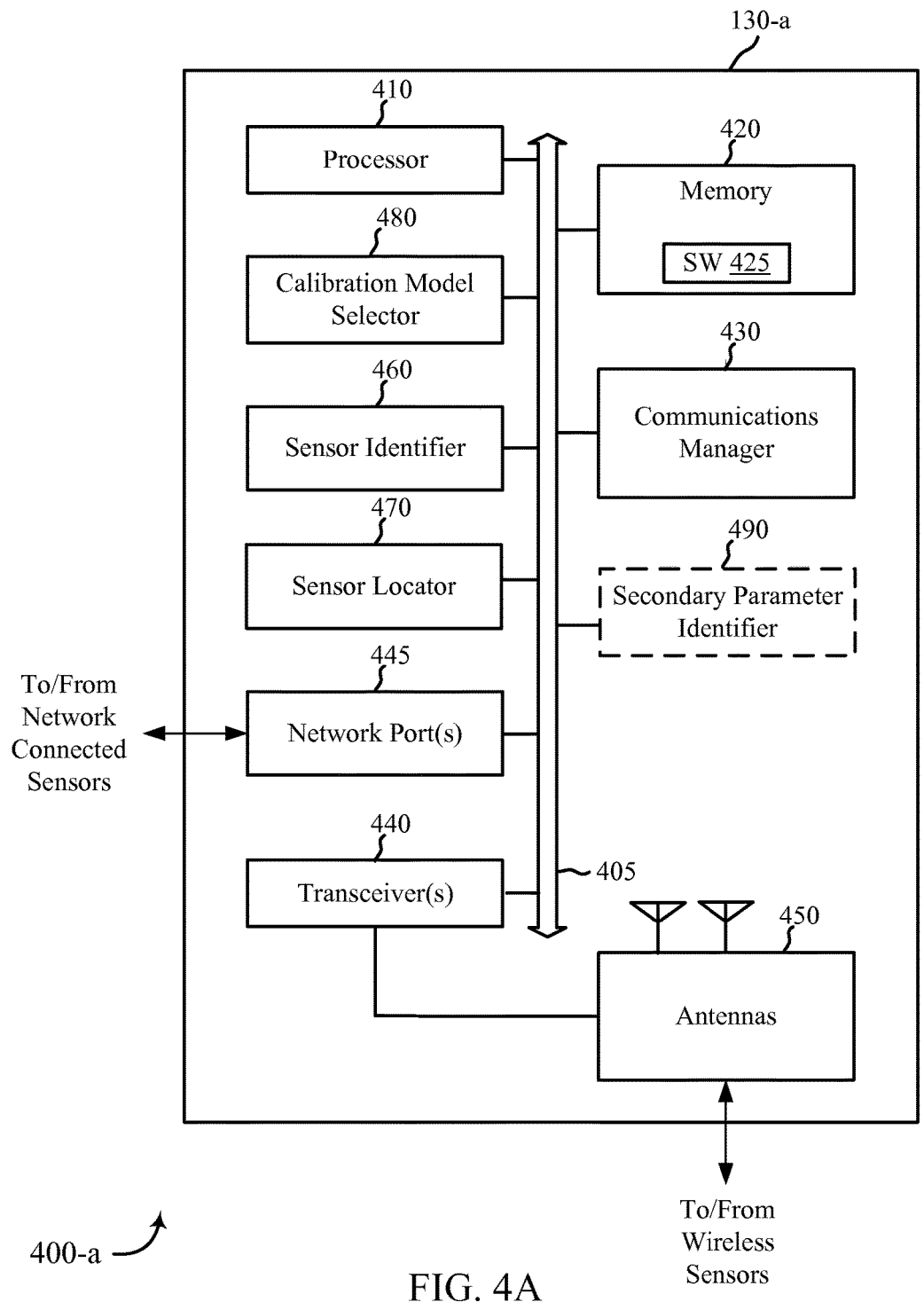
FIG. 4A shows a block diagram of an example of a device configured for use in calibrating a sensor of a distributed sensor system, in accordance with various aspects of the present disclosure.

Turning to FIG. 4A, block diagram 400-*a* is shown that illustrates a calibration device 130-*a* for use in calibrating one or more sensors 111 of a distributed sensor system 100, in accordance with various aspects of the present disclosure. The calibration device 130-*a* may have various other configurations and may be included or be part of a personal computer (e.g., laptop computer, netbook computer, tablet computer, etc.), a cellular telephone, a PDA, an internet appliance, a server, etc. The calibration device 130-*a* can have an internal power supply (not shown), such as a small battery or a solar panel, to facilitate mobile operation, or may be powered via a another source such as a conventional electrical outlet (not shown) when employed in a more stationary fashion (e.g., in an office building). The calibration device 130-*a* is an example of the calibration device 130 of FIG.1 and may perform calibration operations such as described herein with respect to FIGS. 1, 2, 3A, 3B and/or 3C or in accordance with aspects of the method described with respect to FIG. 5.

As shown, the calibration device 130-*a* may include a processor 410, a memory 420, one or more transceivers 440 and/or one or more network ports 445, antennas 450, and a communications manager 430. Each of these components may be in communication with each other, directly or indirectly, over at least one bus 405.

The memory 420 can include RAM and ROM. The memory 420 may store computer-readable, computer-executable software (SW) 425 containing instructions that are configured to, when executed, cause the processor 410 to perform various functions described herein for calibrating sensors of a distributed sensor system 100. Alternatively, the software 425 is not directly executable by the processor 410 but is configured to cause a computer (e.g., when compiled and executed) to perform functions described herein.

The processor 410 can include an intelligent hardware device, e.g., a computer processing unit (CPU), a microcontroller, an application-specific integrated circuit (ASIC), a field-programmable gate array (FPGA), etc. The processor 410 may processes information received through the transceiver(s) 440 and/or to be sent to the transceiver(s) 440 for transmission through the antennas 450. Alternatively or additionally, the processor 410 may processes information received through the network port(s) 445 and/or to be sent via the network port(s) 445 to network connected sensors. The processor 410 may handle, alone or in connection with the communications manager 430, various aspects for communicating with the sensors of the distributed sensor system.

The transceiver(s) 440 and the network port(s) may be configured to communicate bi-directionally with the sensor assemblies 110 of the distributed sensor system, such as described with respect to FIG. 1. The transceiver(s) 440 can be implemented as at least one transmitter and at least one separate receiver. While the calibration device 130-*a* can include a single antenna, there are aspects in which the calibration device 130-a includes multiple antennas 450.

The communications manager 430 manages communications with the sensor assemblies 110 of the distributed sensor system 100, for example, including sensor identities, geospatial locations, sensed data, and calibration information (e.g., corrections, adjustments, directionality, etc.). The communications manager 430 may be a component of the calibration device 130-a in communication with some or all of the other components of the calibration device 130-a over the at least one bus 405. Alternatively, functionality of the communications manager 430 can be implemented as a component of the transceiver(s) 440 and/or the network port(s) 445, as a computer program product, and/or as at least one controller element of the processor 410.

According to the architecture of FIG. 4A, the calibration device 130-a further includes a sensor identifier 460, a sensor locator 470, a calibration model selector 480 and a secondary parameter identifier 490, each of which can be controlled by or operate in conjunction with the communications manager 430. The sensor identifier 460 performs various operations and/or procedures for identifying the sensors 111 of the distributed sensor system 100. For example, the sensor identifier 460 may determine, in addition to identity, information regarding the sensors 111 such as sensor type (including the type of data sensed and how such data is sensed (e.g., sensor technology employed), sensor quality and/or quality of sensed data provided, etc.).

The sensor locator 470 may determine locations of the various sensors 111 of the distributed sensor system 100, or may receive locations from the sensor assemblies 110 that include the sensors 111 themselves or from another source (e.g., locations provided based on a particular layout of fixed-location sensors), and then determine a difference in geospatial location between sensors 111 involved in a calibration procedure.

The calibration model selector 480 may operate in conjunction with the sensor locator 470, employing the determined geospatial difference(s) between sensors 111 to determine an appropriate calibration model to be used for calibrating one or more of such sensors 111. The determined calibration model(s) may be implemented by the processor 410 in conjunction with the memory 420 (e.g., storing calibration models in the SW 425 to be executed by the processor 410).

The secondary parameter identifier 490 may be configured to determine whether the sensed data of an identified sensor 111 is affected by a secondary parameter (e.g., temperature). For example, the secondary parameter identifier 490 may determine a secondary parameter based at least in part on the type of data sensed and/or the technology employed for the sensor 111. Once identified, the processor 410 may adjust or correct the sensed data associated with the sensor 111 to mitigate the effect of the secondary parameter on the sensed data, for example, by implementing an adjustment procedure stored in the memory 420.

Thus, the components of the calibration device 130-a may be configured to implement aspects discussed above with respect to FIGS. 1, 2, 3A, 3B and 3C. Moreover, the components of the calibration device 130-a may be configured to implement aspects discussed below with respect to FIG. 5, and those aspects may not be repeated here for the sake of brevity.

Figure 4B:
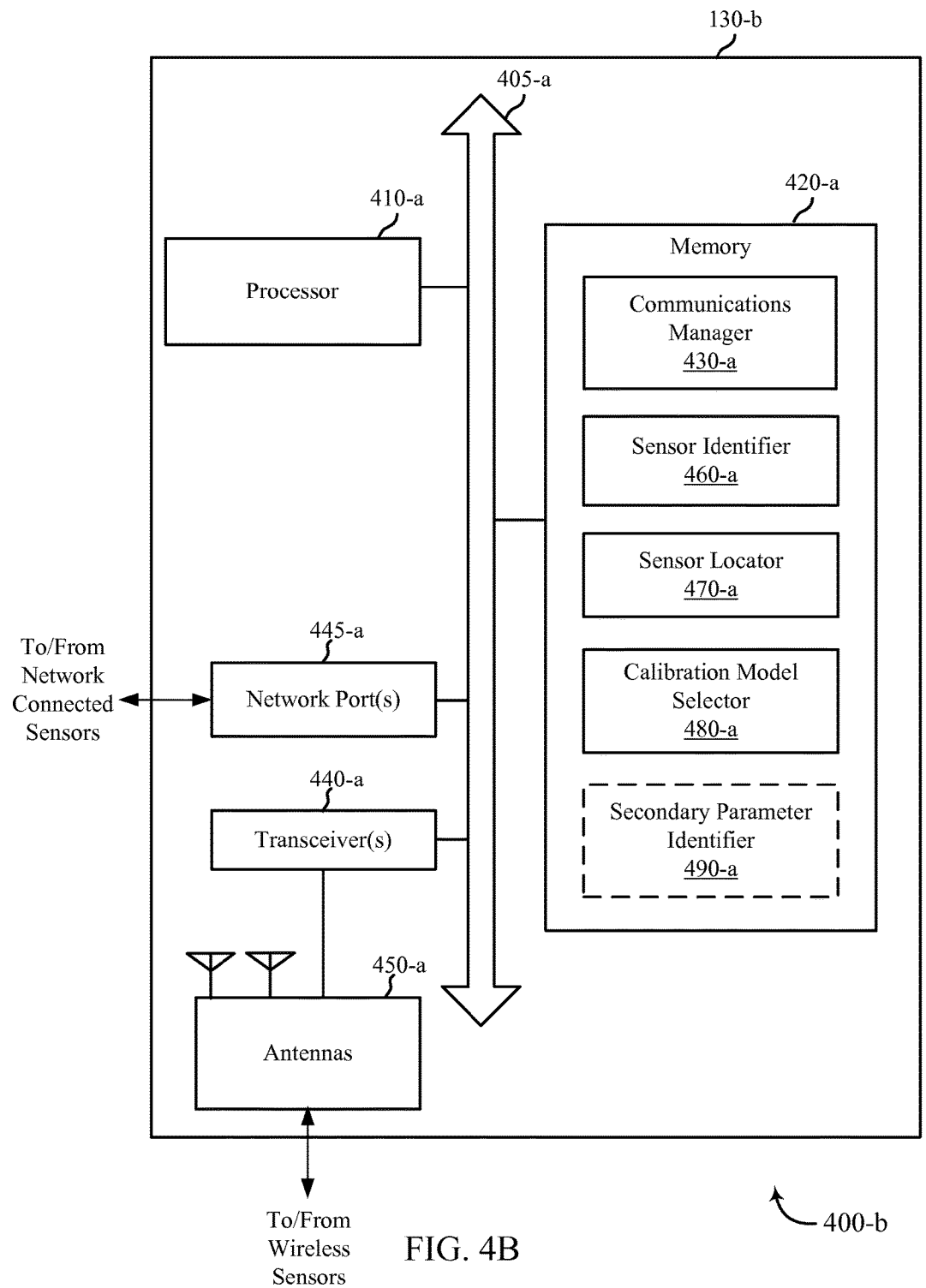
FIG. 4B shows a block diagram of an example of a device configured for use in calibrating a sensor of a distributed sensor system, in accordance with various aspects of the present disclosure.

FIG. 4B shows a block diagram 400-b that illustrates a calibration device 130-b for use in calibrating one or more sensors 111 of a distributed sensor system 100, in accordance with various aspects of the present disclosure. The calibration device 130-b is another example of the calibration devices 130 of FIGS. 1 and 4A, and may implement various aspects described with reference to FIGS. 2, 3A, 3B, 3C and 5. As shown, the calibration device 130-b includes a processor 410-a, a memory 420-a, at least one transceiver 440-a, at least one network port 445-a and at least one antenna 450-a. Each of these components are in communication, directly or indirectly, with one another (e.g., over a bus 405-a). Each of these components may perform the functions described above with reference to FIG. 4A.

In this example, the memory 420-a includes software that performs the functionality of a communications manager 430-a, a sensor identifier 460-a, a sensor locator 470-a and a calibration model selector 480-a. The memory 420-a optionally may include a secondary parameter identifier 490-a. For example, memory 420-a includes software that, when compiled and executed, causes the processor 410-a (or other components of the calibration device 130-b) to perform the functionality described above and further below. A subset of the functionality of the communications manager 430-a, the sensor identifier 460-a, the sensor locator 470-a, the calibration model selector 480-a can be included in memory 420-a; alternatively, all such functionality can be implemented as software executed by the processor 410-a to cause the calibration device 130-b to perform such functions. Other combinations of hardware/software can be used to perform the functions of the communications manager 430-a, the sensor identifier 460-a, the sensor locator 470-a, the calibration model selector 480-a, and/or the secondary parameter identifier 490-a.

Figure 5:
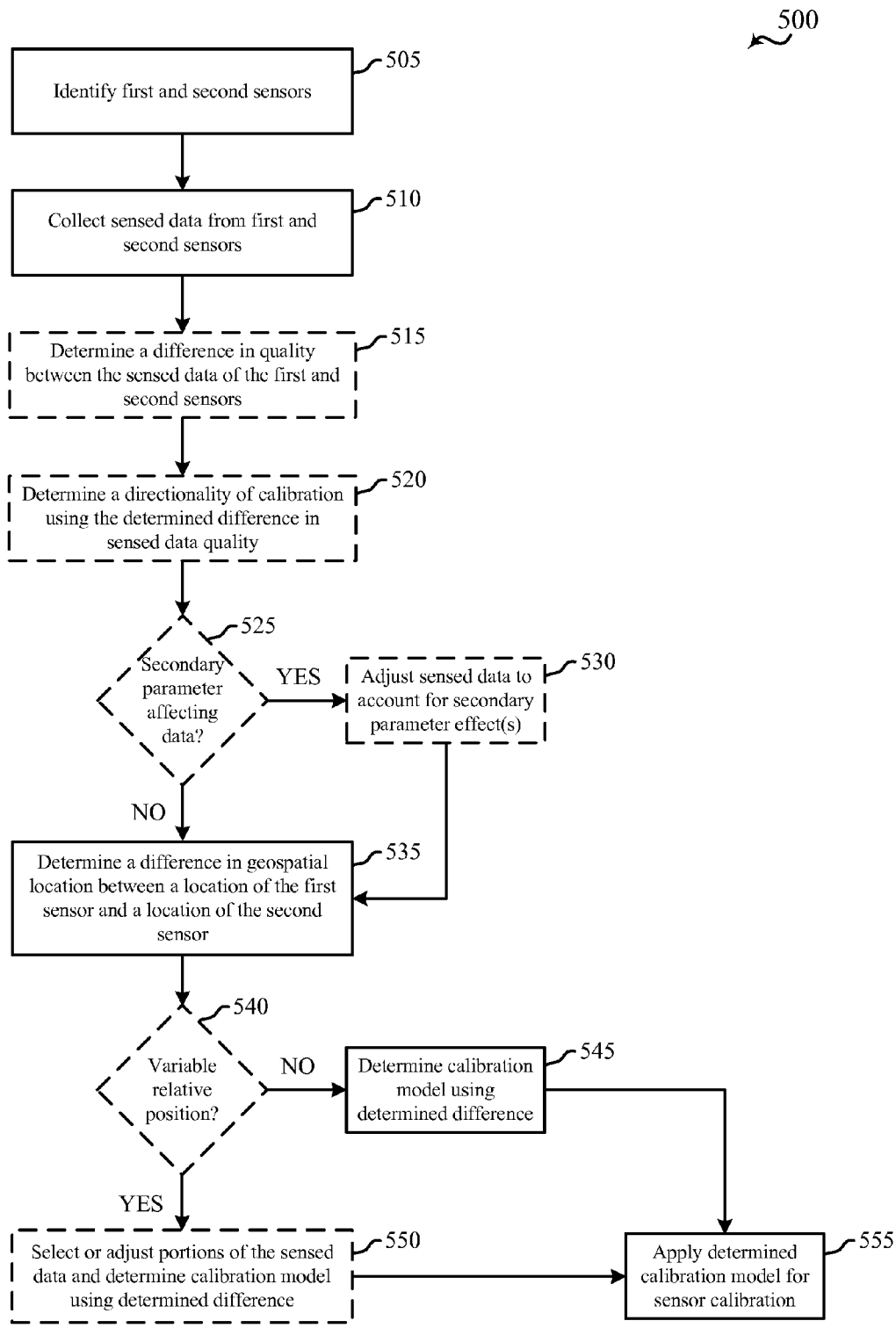
FIG. 5 is a flow chart illustrating an example of a method for calibrating a sensor of a distributed sensor system, in accordance with various aspects of the present disclosure.

FIG. 5 is a flow chart illustrating an example of a method 500 for distributed sensor calibration, in accordance with aspects of the present disclosure. The method 500 may be performed by any of the calibration devices 130 as described with reference to FIGS. 1, 2, 3A, 3B, 4A, or 4B. Broadly speaking, the method 500 illustrates a procedure by which a calibration device 130 performs distributed sensor calibration.

At block 505 the calibration device 130 may identify first and second sensors 111. The first and second sensors 111 may be configured to measure an environmental condition, such as a concentration or partial pressure of oxygen, carbon monoxide, carbon dioxide, sulfur dioxide, nitrogen oxides, water, and the like. Alternatively, the first and second sensors 111 may be configured to measure a broader condition such as temperature, pressure, or density. Alternatively, the first and second sensors 111 may be configured to measure another environmental constituent, such as an atmospheric particulate concentration.

The first and second sensors 111 may be configured to measure an environmental condition directly, or indirectly. For example, a sensor 111 may include a thermocouple that can be used to measure temperature relatively directly. In another example, a sensor assembly 110 may have an environmental sensor 111 that relies on multiple sensor elements to calculate an environmental condition, in which case the sensor 111 may be interpreted as measuring the environmental condition indirectly. In various examples, either or both of the first sensor 111 or the second sensor 111 may measure an environmental condition directly or indirectly. Furthermore, the manner in which the first sensor 111 and the second sensor 111 measure an environmental condition may be the same or different.

Identifying a sensor 111 may include identifying a particular first sensor 111 and second sensor 111 from a plurality of sensors 111 identified in information received at the calibration device 130. This information may include sensor serial numbers or IDs, as well as supporting information such as the type of environmental data, the type of the sensor 111, data format, data units, diagnostic information about the sensor 111, and the like. After identifying the first and second sensors, the method 500 may proceed to block 510.

At block 510 the calibration device 130 may collect sensed data of the first and second sensors 111. The sensed data from the first sensor 111 and the sensed data from the second sensor 111 may correspond to the same environmental condition. For instance, the sensed data from each sensor 111 may be a concentration of a particular atmospheric gas, such as carbon dioxide, in parts per million. In some examples, the sensed data from the first sensor 111 and the sensed data from the second sensor 111 may correspond to the same environmental condition, but may be in different formats. For instance, the calibration device 130 may collect data of the first sensor 111 that represents a gas concentration in parts per million, and data from the second sensor 111 that represents a gas concentration in percentage. In some examples the calibration device 130 may collect data of the first sensor 111 that represents a gas concentration in parts per million and collect data of the second sensor 111 that represents a partial pressure. Thus, in various examples the calibration device 130 may perform any of calculations, conversions, or approximations such that the sensed data from the first sensor 111 and the second sensor 111 can be suitably compared or correlated. After collecting sensed data from the first and second sensors 111, the method 500 may proceed to block 510.

At block 515 the calibration device 130 may optionally determine a difference in quality between the sensed data of the first and second sensors 111. As previously described, in various examples a difference in quality may be related to any of a grade or quality of components, an age of components, a level of noise in sensed data, an amount of sensed data, a periodicity or time period of sensed data, a data history, a calibration history, or a predetermined characteristic. After determining a difference in quality between the sensed data from the first and second sensors, the method 500 may proceed to block 520.

At block 520 the calibration device 130 may determine a directionality of calibration using the determined difference in sensed data quality. For example, where sensors 111 can be compared by relative quality, the calibration device may determine the directionality of calibration as using data from a sensor 111 associated with sensed data having higher quality to calibrate a sensor 111 associated with sensed data having a lower quality. In some examples, such as those relating to a periodicity of sensed data, a difference in quality may not refer to sensed data from two sensors 111 as being better or worse, but may instead refer to a particular characteristic of the sensed data. In such examples, the characteristic may be used to indicate a directionality of calibration. In other examples, sensed data of lower quality may still be used to contribute to a calibration, but its effect may be given a reduced weight or significance to a calibration model. After determining a directionality of calibration using the determined difference in sensed data quality, the method 500 may proceed to block 525.

At block 525 the calibration device 130 may identify whether a secondary parameter may be affecting the sensed data. For example, the measurement a sensor 111 configured to measure certain environmental conditions may rely on a secondary measurement, which may be provided to a sensor 111 or a sensor assembly 110 including the sensor 111 by various means. In such examples, the calibration of the associated sensor 111 may rely on measurements of the secondary parameter associated with the first and second sensors 111 being within a certain range of each other. In some examples, the calibration device 130 may include the secondary parameter in the determining a calibration model. If the calibration device 130 identifies that a secondary parameter may be affecting the sensed data, the method 500 may proceed to block 530. If the calibration device 130 does not identify a secondary parameter may be affecting the sensed data, the calibration device may proceed directly to block 535.

At block 530 the calibration device 130 may adjust sensed data from one or both of the first sensor 111 or the second sensor 111 based on a secondary parameter. For instance, the calibration device 130 may collect a secondary parameter measured by or otherwise provided by a sensor assembly 110 including the sensor 111, or from any other source, and adjust the sensed data from that sensor 111 based on the secondary parameter. In various examples the adjustment may be a conversion of the sensed data based on the secondary parameter, a filtering of the data based on the secondary parameter, or a selection of one or more portions of the sensed data based on the secondary parameter. In some examples, the secondary parameter may be used to select a particular portion of a calibration model, such as a calibration within a particular temperature band, a calibration within a particular pressure band, a calibration within a particular time band, and so on. After adjusting the sensed data to account for the secondary parameter effects, the method 500 may proceed to block 535.

At block 535 the calibration device 130 may determine a difference in geospatial location between a location of the first sensor 111 and a location of the second sensor 111. In some examples, determining the difference in location between the sensors 111 may include determining the location of each of the first sensor 111 and the second sensor 111. In some examples the calibration device 130 may determine a location of a sensor 111 by looking up a predetermined location stored in memory associated with the calibration device 130. In some examples the calibration device may receive information associated with the location of the sensor 111, which may be received from a database at a central processing device 115 or received from a sensor assembly 110 that includes the sensor 111. In examples where a sensor assembly 110 transmits location information, the location information may be predetermined information stored at the sensor assembly 110, or may be otherwise measured by the sensor assembly 110. For instance, in some examples the sensor assembly 110 may be configured to determine a location or a sensor 111 by receiving signals from a GPS or GLONASS satellite constellation, or any other terrestrial or satellite-based system that provides signals that can be used for positioning. In various examples, the location of the sensor 111 as determined by a sensor assembly 110 can be transmitted to the calibration device 130 by a wired or wireless communication link 135.

In some examples, the difference in geospatial location between the first sensor 111 and the second sensor 111 may be a one-dimensional distance value. In some examples the difference in geospatial location may be a two- or three-dimensional value, such as a vector. For instance, the difference in geospatial location may reflect a two-dimensional projection of distance at a reference elevation or altitude, such as at sea level or any other elevation or altitude. A two-dimensional projection may be characterized by a difference in latitude and longitude, a difference in distance in a north-south direction and a distance in an east-west direction, a vector having a distance magnitude and a cardinal direction, or any other suitable two-dimensional representation. A three-dimensional difference in geospatial location may be characterized by a difference in latitude, longitude, and elevation, a vector having a distance magnitude and angles in two principal directions, or any other suitable three-dimensional representation. After determining a difference in geospatial location between a location of the first sensor and a location of the second sensor, the method 500 may proceed to block 540.

At block 540 the calibration device 130 may identify whether the first sensor 111 and the second sensor 111 are separated by a variable relative position. For instance, one or both of the first sensor 111 or the second sensor 111 may be moving, in which case the relative position between them may change. In some examples, the calibration device 130 may simply identify that the distance between the first sensor 111 and the second sensor 111 changes over time. In some examples, the calibration device may determine that both a distance and an orientation from the first sensor 111 to the second sensor 111 has changed. In either case, if the calibration device has identified that the first sensor 111 and the second sensor 111 are separated by a variable relative position, the method 500 may proceed from block 540 to block 555. If no change in relative position is identified, the method may proceed to block 545. At block 545, the method 500 can include determining a calibration model using the determined difference in geospatial location between the first and second sensors 111. For instance, as previously described the calibration device 130 may apply low-pass filtering to sensed data from one of both of the first and second sensors 111 based on the distance between sensors 111, and then use a correlation between the filtered data from the first and second sensors 111 to determine a calibration model. In other examples, the calibration device may modify portions of the sensed data based on a relative orientation between the first sensor 111 and the second sensor 111. For example, the calibration device 130 may have data or other understanding of a prevailing wind or some other source that may be affecting an environmental condition, and may impose a time offset or other phase lag to sensed data corresponding to an environmental measurement from one or both of the first sensor 111 or second sensor 111, and use a correlation of the adjusted data to determine a calibration model.

In some examples, determining a calibration model may include rejecting at least a portion of the data entirely from a calibration. For example, data collected from a sensor 111 may be rejected from a calibration model if the sensor 111 is too far from a target sensor 111 to be calibrated. In some examples, the calibration device 130 may reject data based on identifying or suspecting an error condition associated with the sensor 111. Such identified or suspected error conditions may include an identified drop-out, a sensor "railed" to an output limit, an output that is erroneously locked at an output value, an output that is drifting away from a plausible value, an erratic or noisy output, and the like.

Determining a calibration model may include various means of correlation between data associated with the first and second sensors 111, and adjustment of parameters associated with one or both of the first or second sensors 111. For instance, the calibration device 130 may identify that data for an environmental condition associated with the first sensor 111 is lower than data for the environmental condition associated with the second sensor 111. The calibration device 130 may have various information or criteria to suggest that the first and second sensors 111 should be more closely correlated than their transmitted data may suggest. Therefore, the calibration device 130 may determine a calibration model that includes increasing a sensor gain or sensor offset associated with the first sensor. After determining the calibration model using the determined difference, the method 500 can proceed to block 555.

At block 550, in examples where the calibration device 130 has determined a variable relative position between the first and second sensors, the method 500 can include selecting or adjusting portions of the sensed data and determining a calibration model using the determined difference in geospatial location between the first and second sensors 111.

For example, when applying a frequency-based decomposition or filtering as part of the calibration model, a low-pass filter cutoff frequency may be higher for portions of the data where the sensors 111 are more closely located, and a low-pass filter cutoff frequency may be lower for portions of the data where the sensors 111 are located farther apart. If the distance between the first sensor 111 and the second sensor 111 is greater than a threshold value, portions of the sensed data may be ignored altogether.

In examples where the relative orientation between the first and second sensor 111 changes with respect to the direction of prevailing wind, the calibration device 130 may apply a different time offset or phase lag to each sensor during various portions of the sensed data. In this way, measurements of transient phenomena can be more accurately aligned, providing a more accurate set of data for calibration.

Following the selection or adjustment of portions of the sensed data, the calibration device 130 can apply any of the techniques previously described to determine a calibration model. For instance, the calibration device 130 may determine adjustments to be applied to the calibration of the first sensor 111, such as an adjustment to a sensor gain, a sensor offset, or any other parameter used to convert a physical measurement taken by the sensor 111 to data representing the environmental condition. After selecting portions of the sensed data and determining the calibration model using the determined difference, the method 500 can proceed to block 555.

At block 555, the calibration device 130 may apply the determined calibration model for sensor calibration. As previously described, the calibration model may be applied directly at a sensor 111, at a portion of a sensor assembly 110 that contains the sensor 111, or at any other device that receives sensed data from the sensor, such as a central processing device 115 or other data acquisition unit. Thus, the calibration device 130 may send an instruction to adjust a computational parameter that converts a physical sensor measurement to environmental condition data, with the instruction sent to any one or more of these devices.

The calibration device 130 may additionally provide any one or more of these devices with at least a portion of the calibration model as necessary to improve the correlation of sensors 111 in the distributed sensor system 100. For instance, upon receiving at least a portion of a calibration model, a sensor 111, a sensor assembly 110, or a central processing device 115 can make an adjustment to a sensor gain, sensor offset, or any other parameter that converts a physical measurement into useful data representing the measured environmental condition. In some examples, calibration information for a plurality of sensors 111 may be communicated by the calibration device 130 to a central processing device 115, and the central processing device 115 can use calibration information for the plurality of sensors 111 to adjust sensed data from the plurality of sensors 111 to improve correlation in the distributed sensor system 100.

Thus, the method 500 provides for calibrating a sensor 111 in a distributed sensor system 100. It should be noted that the method 500 is just one implementation and that the operations of the method 500 can be rearranged or otherwise modified such that other implementations are possible. For example, blocks 515 and 520, blocks 525 and 530, and blocks 540 and 550 as depicted in dashed lines may be optional. For example, blocks 515 and 520 may be omitted if the calibration is performed on both the first sensor and the second sensor. Further, if both the first sensor and the second sensor are stationary (e.g., fixed in location), then blocks 540 and 550 may be omitted.

Furthermore, although the method 500 is described with reference to a first sensor 111 and a second sensor 111, it should be appreciated that a distributed sensor calibration may be performed between any number of sensors. For example, a calibration device may identify a plurality of sensors 111, collect data of the plurality of sensors 111, and determine a calibration model based on the plurality of sensors 111. The calibration device may apply weighting to the sensed data collected from individual sensors 111 based on such factors as a location of the sensors 111 or a difference in location between various individual sensors 111 and a sensor 111 to be calibrated.

The detailed description set forth above in connection with the appended drawings describes examples and does not represent the only examples that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and apparatuses are shown in block diagram form in order to avoid obscuring the concepts of the described examples.

Information and signals may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and components described in connection with the disclosure herein may be implemented or performed with a general-purpose processor, a digital signal processor (DSP), an application-specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, multiple microprocessors, one or more microprocessors in conjunction with a DSP core, or any other such configuration.

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope and spirit of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

Computer-readable media includes both computer storage media and communication media including any medium that facilitates transfer of a computer program from one place to another. A storage medium may be any available medium that can be accessed by a general purpose or special purpose computer. By way of example, and not limitation, computer-readable media can comprise RAM, ROM, EEPROM, flash memory, CD-ROM or other optical disk storage, magnetic disk storage or other magnetic storage devices, or any other medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include compact disc (CD), laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed herein.

What is claimed is:

1. A method for calibrating an environmental sensor of a distributed environmental sensor system by a calibration device, the method comprising;

collecting sensed data of a first environmental sensor and a second environmental sensor of the distributed environmental sensor system;

determining a difference in geospatial location between a location of the first environmental sensor and a location of the second environmental sensor;

determining a difference between a quality of the sensed data of the first environmental sensor and a quality of the sensed data of the second environmental sensor;

determining a calibration model that is based at least in part on the determined difference in geospatial location and the determined difference between the quality of the sensed data of the first environmental sensor and the quality of the sensed data of the second environmental sensor; and calibrating the first environmental sensor using the determined calibration model and the sensed data of the second environmental sensor.

2. The method of claim 1, wherein calibrating the first environmental sensor comprises:

sending an instruction to adjust a computational parameter that converts a physical sensor measurement to environmental condition data, wherein the instruction is sent to any one or more of: the first environmental sensor, an assembly that includes the first environmental sensor, or a device that receives data from the first environmental sensor.

3. The method of claim 1, wherein calibrating the first environmental sensor comprises:

correlating the sensed data of the first environmental sensor with the sensed data of the second environmental sensor.

4. The method of claim 3, wherein calibrating the first environmental sensor comprises:

performing a frequency-based decomposition of the sensed data of the first and second environmental sensors that is based at least in part on the determined difference in geospatial location.

5. The method of claim 4, wherein determining the calibration model comprises:

selecting a portion of the decomposed data of the first environmental sensor and a portion of the decomposed data of the second environmental sensor, wherein the selection is based at least in part on the determined difference in geospatial location.

6. The method of claim 5, herein calibrating the first environmental sensor comprises:

correlating the selected portions of the decomposed data of the first and second environmental sensors.

7. The method of claim 1, wherein determining the calibration model comprises:

determining a weight of the sensed data of the second environment sensor for the determined calibration model based at least in part on the determined difference in geospatial location or the determined difference between the quality of the sensed data of the first environmental sensor and the quality of the sensed data of the second environmental sensor.

8. The method of claim 1, further comprising:

determining to calibrate the first environmental sensor when the quality of the sensed data of the first environmental sensor is lower than the quality of the sensed data of the second environmental sensor.

9. The method of claim 1, wherein the quality of the sensed data of at least one of the first environmental sensor and the second environmental sensor is based at least in part on an amount of the sensed data provided by that environmental sensor, a data history of that environmental sensor, a periodicity of data provided by that environmental sensor assembly, a calibration history of that environmental sensor, or a predetermined characteristic of that environmental sensor, or a combination thereof.

10. The method of claim 1, wherein calibrating the first environmental sensor comprises:

selecting a portion of the sensed data of the first environmental sensor and a corresponding portion of the sensed data of the second environmental sensor based at least in part on the determined difference in geospatial location over time.

11. The method of claim 1, further comprising:

determining a parameter that affects the sensed data of the first environmental sensor; and adjusting the sensed data of the first environmental sensor based on an effect of the parameter, the adjustment being performed prior to performing the calibration.

12. The method of claim 1, further comprising:

calibrating the second environmental sensor using the determined calibration model and the sensed data of the first environmental sensor.

13. A device for calibrating an environmental sensor of a distributed environmental sensor system, the device comprising:

a processor and memory communicatively coupled to the processor, the memory comprising computer-readable code that, when executed by the processor, causes the device to:

collect sensed data of a first environmental sensor and a second environmental sensor of the distributed environmental sensor system determine a difference in geospatial location between a location of the first environmental sensor and a location of the second environmental sensor;

determine a difference between a quality of the sensed data of the first environmental sensor and a quality of the sensed data of the second environmental sensor;

determine a calibration model that is based at least in part on the determined difference in geospatial location and the determined difference between the quality of the sensed data of the first environmental sensor and the quality of the sensed data of the second environmental sensor; and calibrate the first environmental sensor using the determined calibration model and the sensed data of the second environmental sensor.

14. The device of claim 13, wherein the memory further comprises computer-readable code that, when executed by the processor, causes the device to calibrate the first environmental sensor by:

sending an instruction to adjust a computational parameter that converts a physical sensor measurement to environmental condition data, wherein the instruction is sent to any one of: the first environmental sensor, an assembly that includes the first environmental sensor, or a device that receives data from the first environmental sensor.

15. The device of claim 13, wherein the memory further comprises computer-readable code that, when executed by the processor, causes the device to calibrate the first environmental sensor by:

correlating the sensed data of the first environmental sensor with the sensed data of the second environmental sensor.

16. The device of claim 15, wherein the memory further comprises computer-readable code that, when executed by the processor, causes the device to calibrate the first environmental sensor by:

performing a frequency-based decomposition of the sensed data of the first and second environmental sensors that is based at least in part on the determined difference in geospatial location.

17. The device of claim 13, wherein the computer-readable code to determine the calibration model is configured to:

determine a weight of the sensed data of the second environmental sensor for the determined calibration model based at least in part on the determined difference in geospatial location or the determined difference between the quality of the sensed data of the first environmental sensor and the quality of the sensed data of the second environmental sensor.

18. The device of claim 13, wherein the memory further comprises computer-readable code that, when executed by the processor, causes the device to:

determine to calibrate the first environmental sensor when the quality of the sensed data of the first environmental sensor is lower than the quality of the sensed data of the second environmental sensor.

19. The device of claim 13, wherein the quality of the sensed data of at least one of the first environmental sensor and the second environmental sensor is based at least in part on an amount of the sensed data provided by that environmental sensor, a data history of that environmental sensor, a periodicity of data provided by that environmental sensor assembly, a calibration history of that environmental sensor, or a predetermined characteristic of that environmental sensor, or a combination thereof.

20. A non-transitory computer-readable medium comprising computer-readable code that, when executed, causes a device to:

collect sensed data of a first environmental sensor and a second environmental sensor of a distributed environmental sensor system;

determine a difference in geospatial location between a location of the first environmental sensor and a location of the second environmental sensor;

determine a difference between a quality of the sensed data of the first environmental sensor and a quality of the sensed data of the second environmental sensor;

determine a calibration model that is based at least in part on the determined difference in geospatial location and the determined difference between the quality of the sensed data of the environmental sensor and the quality of the sensed data of the second environmental sensor; and calibrate the first environmental sensor using the determined calibration model and the sensed data of the second environmental sensor.

* * * * *